United States Patent [19]
Werner

[11] B 3,992,440
[45] Nov. 16, 1976

[54] 4-ETHERS OF 3-AMINO-5-SULFAMOYLBENZOIC ACIDS

[75] Inventor: Lincoln Harvey Werner, Summit, N.J.

[73] Assignee: Ciba-Geigy Corporation, Ardsley, N.Y.

[22] Filed: Aug. 8, 1973

[21] Appl. No.: 386,828

[44] Published under the second Trial Voluntary Protest Program on February 3, 1976 as document No. B 386,828.

Related U.S. Application Data

[63] Continuation-in-part of Ser. No. 297,530, Oct. 13, 1972.

[52] U.S. Cl. .................... 260/516; 260/247.1 R; 260/268 TR; 260/293.72; 260/293.81; 260/293.83; 260/326.82; 260/332.2 R; 260/347.2; 260/470; 260/519; 424/248; 424/250; 424/267; 424/274; 424/275; 424/278; 424/310; 424/319

[51] Int. Cl.² .................................. C07C 143/80

[58] Field of Search ............... 260/470, 516, 519

[56] References Cited
UNITED STATES PATENTS

| | | | |
|---|---|---|---|
| 3,567,714 | 3/1971 | Wilson | 260/470 |
| 3,706,790 | 12/1972 | Sprague et al. | 260/470 |
| 3,806,534 | 4/1974 | Feit | 260/519 |

*Primary Examiner*—John F. Terapane
*Attorney, Agent, or Firm*—Joseph G. Kolodny; Theodore O. Groeger; John J. Maitner

[57] ABSTRACT

4-Phenylethers of 3-amino-5-sulfamoylbenzoic acids, e.g. those of the formula

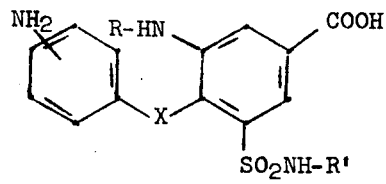

R = an aliphatic or araliphatic radical
X = O or S
R' = H, alkyl or aminophenyl alkyl esters or salts thereof are diuretic agents.

7 Claims, No Drawings

4-ETHERS OF 3-AMINO-5-SULFAMOYLBENZOIC ACIDS

CROSS-REFERENCE TO RELATED APPLICATION

This is a continuation-in-part of application Ser. No. 297,530, filed Oct. 13, 1972.

BACKGROUND OF THE INVENTION

Pursuant to the discovery of the diuretic 4-halo-5-sulfamoyl-anthranilic acids, substituted at the sulfamoyl moiety by an araliphatic or aromatic radical, described in my U.S. Pat. Nos. 3,565,920 or 3,658,990, there was generated a new class of primary amino compounds herein described, which members surprisingly do not require a halogen atom or a tertiary amino group at the aromatic nucleus, thought to be essential for diuretics, such as the chlorothiazides, hydrochlorothiazides or said anthranilic acids, or the sulfamoylbenzoic acids described in U.S. Pat. Nos. 2,937,169 and 3,163,645 or Belgian Pat. No. 743,744 respectively.

SUMMARY OF THE INVENTION

The present invention concerns and has for its object the provision of new 4-phenylethers of 3-amino-5-sulfamoylbenzoic acids and the lower alkyl esters and therapeutically acceptable salts thereof, more particularly of those corresponding to

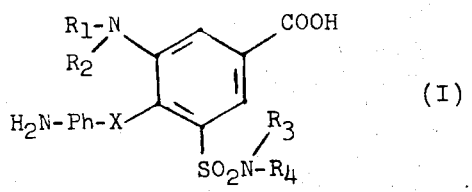

(I)

in which $R_1$ is an aliphatic or araliphatic radical, $R_2$ is hydrogen or an aliphatic radical, $R_3$ is hydrogen or lower alkyl, X is oxygen or sulfur, Ph is a phenylene radical and $R_4$ is hydrogen, lower alkyl or Ph—$NH_2$, or the lower alkyl esters or therapeutically useful ammonium, alkali or alkaline earth metal or acid addition salts thereof, as well as of corresponding pharmaceutical compositions and of methods for the preparation and application of these products, which are useful, orally applicable diuretic, natri- and chloriuretic agents.

DESCRIPTION OF THE PREFERRED EMBODIMENTS

An aliphatic radical $R_1$ or $R_2$ is, for example, lower alkyl, e.g. methyl, ethyl, n- or i-propyl, n-, i- or sec. butyl, n or i-pentyl, neopentyl, n-hexyl or n-heptyl; lower alkenyl, e.g. allyl, methallyl or 2-butenyl; lower alkynyl, e.g. propargyl; mono- or bicyclic cycloalkyl, cycloalkenyl, cycloalkyl-lower alkyl or cycloalkenyl-lower alkyl with preferably 3 to 7 ring-carbon atoms, 1 to 4 chain carbon atoms and optional, e.g. up to 4, lower alkyl groups, e.g. cyclopropyl, 2,3-dimethyl cyclopropyl, cyclobutyl, cyclopentyl, 2- or 3-methyl-cyclopentyl, 2,5- or 3,4-dimethyl-cyclopentyl, cyclohexyl, 2-, 3- or 4-methyl-cyclohexyl, 2,3- 2,4- or 3,5-dimethyl-cyclohexyl, 2,4,6-trimethylcyclohexyl, cycloheptyl, cyclooctyl, 2- or 7-norbornanyl, 1- or 2-decahydronaphthyl; 1- or 2-cyclopentenyl, 2,4-cyclopentadienyl, 2- or 3-methyl-2-cyclopentenyl, 4,5-dimethyl-2-cyclopentenyl, 1-,2- or 3-cyclohexenyl, 2,5-cyclohexadienyl, 2-, 3- or 4-methyl-1- or 2-cyclohexenyl, 2,4 or 3,5-dimethyl-1- or 2-cyclohexenyl, 2,4,6-trimethyl-2,5-cyclohexadienyl, 1-, 2- or 3-cycloheptenyl, 2,6-cycloheptadienyl, 2-cyclooctenyl or 2-norborn-5-enyl; as well as the corresponding cycloalkyl- or cycloalkenyl-lower alkyl groups in which the chain especially represents methyl, but also ethyl,n- or i-propyl, n-, i- or sec. butyl; it contains in any of the positions available for substitution one of the specific cycloalkyl or cycloalkenyl groups listed above. The term "lower", referred to above and hereinafter in connection with organic radicals or compounds respectively, defines such with up to 7, preferably up to 4, carbon atoms.

Said aliphatic radicals, especially the lower alkyl groups $R_1$ can be substituted, e.g. by free or functionally converted hydroxy, mercapto or carboxy groups and/or interrupted by heteroatoms, e.g. one oxygen, sulfur and/or nitrogen atom, and are represented, for example, by lower haloalkyl, e.g. 2-(chloro, bromo or iodo)-ethyl, 3,3-difluoro- or dichloropropyl, 3,3,3-trichloropropyl, 3- or 4-chlorobutyl, 4,4- or 3,4-dichlorobutyl or 4,4,4-trifluorobutyl; unsubstituted or halogenated lower alkoxy- or alkylmercapto-lower alkyl, such as 2-ethoxyethyl, 3-methoxypropyl, 2-ethylmercapto-ethyl, 2-(2,2-dichloroethoxy)-ethyl, 2-(2-chloroethoxy-ethyl, 2-(2,2,2-trifluoroethylmercapto)-ethyl or 2-(2,2′-dichloroethylmercapto)-ethyl; carbamyl-lower alkyl or N,N-di lower alkylcarbamyl-lower alkyl, such as carbamyl-methyl, N,N-dimethylcarbamyl-methyl, 2-carbamyl-ethyl or 2-N,N-diethyl-carbamyl-ethyl; sec. or tert. amino-lower alkyl, such as mono- or di-lower alkylamino-lower alkyl, lower alkyleneimino-lower alkyl, lower monoaza-, -oxa- or -thiaalkyleneimino-lower alkyl or N-lower alkyl-lower monoazaalkyleneimino-lower alkyl, e.g. 2-ethylamino-ethyl, 2-dimethylamino-ethyl, 3-diethylamino-propyl, 2-pyrrolidino-ethyl, 2-piperidino-ethyl, 2-(4-methyl-piperazino)-ethyl or 2-morpholino-ethyl; 5 to 7 ring-membered oxa-cycloalkyl or -cycloalkenyl, oxa-cycloalkyl- or -cycloalkenyl-lower alkyl, such as 3-tetrahydrofuryl, tetrahydrofuryl-2-methyl, (2-methyltetrahydrofuryl-2)-methyl, 2,3-dihydro- or tetrahydropyranyl-2-methyl.

An araliphatic radical $R_1$ preferably represents H-Ph-lower alkyl or -alkenyl or Hc-lower alkyl or -alkenyl, in which the alkyl or alkenyl moiety preferably has up to 4 chain carbon atoms. Ph is a phenylene radical, which is unsubstituted or substituted by one or more than one, preferably one or two substituents selected, for example, from lower alkyl, e.g. that mentioned above, free or functionally converted hydroxy or mercapto, such as lower alkoxy, lower alkylenedioxy, lower alkylmercapto or halogeno, e.g. methoxy, ethoxy, n- or i-propoxy or -butoxy; methylenedioxy, 1,1- or 1,2-ethylenedioxy; methyl- or ethylmercapto; fluoro, chloro or bromo; (hydroxy or halogeno)-lower alkyl or -alkoxy, e.g. 2-hydroxyethyl, trifluoromethyl or 2-hydroxyethoxy; nitro; amino, especially di-lower alkylamino, e.g. dimethylamino or diethylamino; or free or functionally converted carboxy or sulfo e.g. lower carbalkoxy, carbamoyl, cyano or sulfamoyl. Hc is either unsubstituted pyridyl, furyl or thienyl, or such radical substituted by one or more than one, preferably one or two lower alkyl groups.

Preferred araliphatic or aromatic radicals $R_1$, $R_4$ and $H_2N-Ph$ are represented by the formulae $H-Ph'-C_mH_{2m}$, $Hc'-C_mH_{2m}$ and $H_2N-Ph'-C_mH_{2m}$ respectively, wherein $Ph'$ is unsubstituted 1,2-phenylene, advantageously 1,3-phenylene or preferably 1,4-phenylene, or such radicals substituted by one member of the group consisting of lower alkyl, hydroxy, lower alkoxy, halogeno or trifluoromethyl; $Hc'$ is unsubstituted 2-, 3-, or 4-pyridyl, 2- or 3-furyl or -thienyl, or such radicals substituted by one or two lower alkyl groups and $m$ is an integer from 0 to 4.

Each of $R_2$, $R_3$ and $R_4$ is preferably hydrogen, but also lower alkyl, e.g. that mentioned above, advantageously methyl, $R_2$, moreover, represents lower alkenyl or alkynyl, also mentioned above, especially 2-butenyl, and $R_5$ may also represent $Ph'-NH_2$.

Preferred esters of the acids of Formula I are the methyl, ethyl, n- or i-propyl or -butyl esters and of the salts the ammonium, sodium potassium, magnesium or calcium salts are preferred. Due to the amino groups present, also acid addition salts can be prepared, e.g. such of the therapeutically useful acids listed below.

The compounds of the invention exhibit valuable pharmacological properties. Primarily they show diuretic, natri- and chloriuretic activity with rapid onset of action, high urine but low potassium excretion levels. This can be demonstrated in animal tests using, for example mammals, e.g. rats or dogs, as test objects. Such tests are performed, for example, by administering the compounds of the invention within a gelatin capsule to dogs, or in the form of aqueous solutions or starchy suspensions by stomach tube to rats, in an oral dosage range between about 0.01 and 50 mg/kg/day, preferably between about 0.1 and 10 mg/kg/day, advantageously between about 0.5 and 5 mg/kg/day. Simultaneously the test animals may receive various salt loads enterally or parenterally, for example, various amounts of subcutaneously applied 0.9% saline, e.g. 100 ml thereof per medium-sized dog (beagle). Urine is then collected, e.g. at 2 hour intervals, with or without catheterization, and its volume, sodium, potassium and chloride content estimated and compared with that of the same untreated or saline-treated animals. Besides the anti-edematous utility, the compounds of the invention can also be used as intermediates in the preparation of other valuable products, primarily of pharmacologically active compounds or compositions, e.g. such useful in the management of hypertension.

Preferred and highly diuretic are those compounds of Formula I in which $R_1$ is lower alkyl, lower alkenyl, lower alkynyl, (monocyclic, 3 to 7 ring-membered cycloalkyl, cycloalkenyl, oxacycloalkyl, 2- or 7-norbornanyl or 2-norborn-5-enyl)-$C_mH_{2m}$; $H-Ph'-C_nH_{2n}$, $H-Ph'-CH=CH-CH_2$, or $Hc'-C_nH_{2n}$ wherein $Ph'$ is 1,2-, 1,3- or 1,4-phenylene, unsubstituted or substituted by one member of lower alkyl, hydroxy, lower alkoxy, halogeno or trifluoromethyl, $Hc'$ is 2-, 3- or 4-pyridyl, 2- or 3-furyl or -thienyl, unsubstituted or substituted by one or two lower alkyl groups, $m$ is an integer from 0 to 4 and $n$ is an integer from 1 to 4, $R_2$ is hydrogen, lower alkyl, lower alkenyl or lower alkynyl, $R_3$ is hydrogen or lower alkyl, X is oxygen or sulfur, Ph is the above $Ph'$ and $R_4$ is hydrogen, lower alkyl or $Ph'-NH_2$, or the lower alkyl esters, or therapeutically useful ammonium, alkali or alkaline earth metal or acid addition salts thereof.

Especially valuable and suitable for said utility are the compounds of Formula II

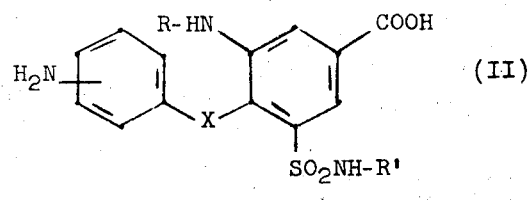

wherein R is alkyl or alkenyl with 3 to 7 carbon atoms, (3 to 7 ring-membered cycloalkyl, tetrahydrofuryl, 2- or 7-norbornanyl, 2-norborn-5-enyl, phenyl tolyl, anisyl, halophenyl, furyl or thienyl)-methyl or -ethyl, or cinnamyl, X is oxygen or sulfur, and R' is hydrogen or aminophenyl, or therapeutically useful ammonium, alkali metal or acid addition salts thereof.

Outstandingly active compounds are those of Formula II, wherein R is alkyl or 2-alkenyl with 4 or 5 carbon atoms, cyclopropylmethyl, 2-tetrahydrofurylmethyl, 2-norborn-5-enylmethyl, benzyl, furfuryl, or cinnamyl, X is oxygen or preferably sulfur, and R' is hydrogen, or therapeutically useful ammonium, alkali metal or acid addition salts thereof.

Most preferred are the 4-(4-aminophenylmercapto)-3-(n- or i-butyl or cyclopropylmethyl)-amino-5-sulfamoylbenzoic acids which, when given to rats or dogs at oral doses as low as 0.3 mg/kg/day, exhibit outstanding diuretic, natri- and chloriuretic effects.

The compounds of the invention are prepared according to methods in themselves known. Advantageously they are obtained by:

a. converting in a compound of Formula III

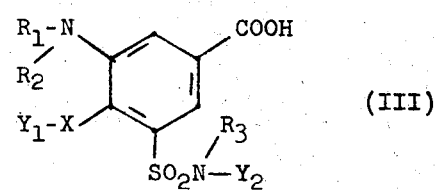

wherein $Y_1$ is an (acylamino, nitro or arylazo)-Ph radical and $Y_2$ is $R_4$ or $Y_1$, or a lower alkyl ester or salt thereof, $Y_1$ and $Y_2$ into the corresponding aminophenyl group by hydrolysis or hydrogenation respectively or b. converting in a compound of Formula IV

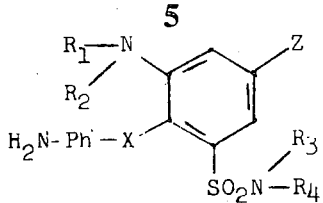

(IV)

wherein Z is a carbamoyl or aminocarbamoyl group, or a salt thereof, Z into carboxy, carbalkoxy or salified carboxy by hydrolysis or alcoholysis, or c. reacting a compound of Formula V

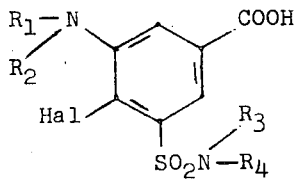

(V)

wherein Hal is a halogen atom, or a lower alkyl ester or salt thereof, with a compound of the formula $H_2N—Ph—XH$ or an alkali metal salt thereof and, if desired, converting any resulting compound into another compound of the invention.

In said compounds of Formula III containing the (acylamino, nitro or arylazo)-Ph radical $Y_1$ and, as the case may be, $Y_2$ also, the acylamino group is advantageously derived from either a lower alkanoic or carbonic acid lower alkyl ester and the arylazo group is preferably that of the formula $H—Ph—N=N—$. Said acylaminophenyl compounds, preferably the (lower alkanoyl- or lower alkoxy carbonylamino)-Ph, e.g. the (acetyl-, propionyl- or ethoxycarbonylamino)-Ph compounds, are converted into the compounds of the invention by hydrolysis, for example, with the use of aqueous bases, such as aqueous alkali metal hydroxides or carbonates or quaternary ammonium hydroxides, e.g. sodium hydroxide, potassium carbonate or trimethylbenzyl-ammonium hydroxide. In case $Y_1$ and $Y_2$ stand for said (nitro or arylazo)-Ph group, it is converted into aminophenyl by conventional reduction, for example, with the use of catalytically activated or nascent hydrogen, e.g. hydrogen in the presence of platinum, palladium or nickel catalysts, e.g. Raney nickel, or generated by the action of non-precious metals, e.g. zinc or iron, on acids, such as mineral acids, e.g. hydrochloric or sulfuric acid, or with the use of reducing agents, preferably salts of elements of the 4th to 6th group of the Periodic Table and being in a low oxidation state, such as stannous or chromous halides, ammonium polysulfides or alkali metal hydrosulfites.

The carbamoyl or aminocarbamoyl group Z in said compounds of Formula IV is preferably unsubstituted, but may also be substituted by lower alkyl, aralkyl or aryl radicals, e.g. $R_1$, Ph—$NH_2$ or $Y_2$. The corresponding amides or hydrazides, e.g. the mono- or dimethylamide, diethylamide, i-propylamide; benzylamide or acetylaminophenylamide, or the corresponding hydrazides, are hydrolysed or alcoholized to the compounds of Formula I, their lower alkyl esters or salts, according to conventional methods, advantageously with the use of aqueous or corresponding alcoholic bases, such as those described above, or lower alkanolic alkali metal alkoxides, e.g. ethanolic sodium ethoxide.

The phenols or thiophenols $H_2N—Ph—XH$ in process (c) are preferably reacted in the form of their alkali metal salts, e.g. the sodium or potassium salts. The halogen atom Hal in the above compounds of Formula V is preferably fluorine, but also chlorine, bromine or iodine.

The compounds of the invention so obtained can be converted into each other according to known methods. For example, resulting compounds in which $R_2$ and/or $R_3$ stand for hydrogen, can be reacted with a reactive ester of the corresponding alcohol, e.g. that of a lower alkanol, for example, derived from a hydrohalic or sulfonic acid, to yield the corresponding mono- or bis-lower alkyl compounds. Resulting unsaturated compounds, e.g. lower alkenyl, alkynyl or furfuryl compounds, can be hydrogenated as shown above, to yield the corresponding saturated, e.g. lower alkyl or tetrahydrofurfuryl compounds. Resulting lower alkyl esters can also be hydrolyzed or transesterified, for example, with the use of the above alkaline hydrolyzing or alcoholizing agents.

The compounds of the invention are obtained in the free form or in the form of their salts, depending on the conditions under which the process is carried out, the salts are also included in the present invention. These are particularly derived from the free acids and therapeutically useful inorganic or organic bases, primarily the alkali metal, alkaline earth metal, e.g. sodium, potassium, magnesium or calcium salts, or ammonium salts derived from ammonia or amines, such as those corresponding to the amino group $R_1—N—R_2$, e.g. mono-, di- or tri-lower alkylamines, -cycloalkylamines, -cycloalkyl-lower alkylamines or -aralkylamines, mixed amines or tertiary nitrogen bases, such as pyridine, collidine or lutidine. Said compounds of Formula I also form acid addition salts, preferably with therapeutically useful acids, such as mineral acids, e.g. hydrochloric, hydrobromic, sulfuric, phosphoric, nitric or perchloric acid; aliphatic or aromatic carboxylic or sulfonic acids, e.g. formic, acetic, propionic, succinic, glycollic, lactic, malic, tartaric, citric, ascorbic, maleic, hydroxymaleic, pyroracemic, phenylacetic, benzoic, 4-aminobenzoic, anthranilic, 4-hydroxybenzoic, salicylic, 4-aminosalicylic, embonic, nicotinic, methanesulfonic, ethanesulfonic, hydroxyethanesulfonic, ethylenesulfonic, halogen-benzenesulfonic, toluenesulfonic, naphthalenesulfonic or sulfanilic acid; methionine, tryptophane, lysine or arginine.

The invention further includes any variant of the present process in which an intermediate product obtainable at any stage of the process is used as starting material and any remaining steps are carried out, or the process is discontinued at any stage thereof, or in which the starting materials are formed under the reaction conditions, for example, amides of Formula IV from nitriles, or in which the reaction components are used in the form of their salts. Mainly those starting materials should be used in the reactions of the invention that lead to the formation of those compounds indicated above as being especially valuable.

The starting material is obtained according to known methods, preferably those illustrated by the examples herein. For example, the compounds of Formula III are obtained by condensing reactive esters of the alcohols $R_1$-OH, e.g. those mentioned above, or corresponding aldehydes, with compounds of the Formual VI

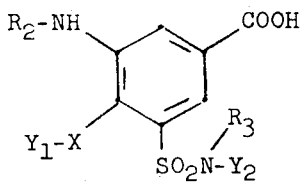

(obtainable according to the methods disclosed in J. Med. Chem., 1971, Vol. 14, No. 5, page 432) and hydrogenating any Schiff's base obtained, e.g. as shown above, or with the use of complex light metal hydrides, such as alkali metal borohydrides, e.g. sodium borohydride. Compounds of Formulae III and IV can also be prepared by reacting corresponding phenols or thiophenols of the formulae $Y_1$—X—H or $H_2N$—Ph—X—H, preferably their alkali metal salts, e.g. sodium or potassium salts, with compounds of the Formula VII

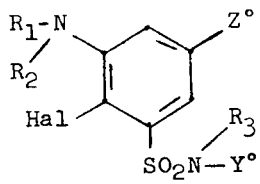

wherein Z° is a free or corresponding esterified or amidated carboxy group or cyano and Y° is either $Y_2$ or $R_4$, and the other symbols have the meaning given above, preferably at elevated temperature and/or pressure. Representative members of said halogenated acids, or lower alkyl esters thereof, are described in J. Med. Chem., 1970, Vol. 13, No. 6, page 1071, showing also various methods according to which the above intermediates can be prepared. The corresponding amides or hydrazides are obtainable from said esters by ammono- or hydrazinolysis, which process may take place simultaneously in the above condensation, when using compounds in which Z° is lower carbalkoxy.

Resulting mixtures of isomers, e.g. of compounds of Formulae I to VII, can be separated into the single isomers by methods in themselves known, e.g. by fractional distillation, crystallization and/or chromatography. Racemic products can likewise be resolved into the optical antipodes, for example by separation or diastereomeric salts thereof, e.g. by the fractional crystallization of d- or l-tartrates or d-α-(phenyl or l-naphthyl)-ethylamine or l-cinchonidine salts.

The above reactions are carried out according to standard methods, in the presence or absence of diluents, preferably such as are inert to the reagents and are solvents thereof, of catalysts, condensing or neutralizing agents and/or inert atmospheres, at low temperatures, room temperature or advantageously elevated temperatures, at atmospheric or superatmospheric pressure.

The pharmacologically active compounds of the invention are useful in the manufacture of pharmaceutical compositions containing an effective amount thereof in conjunction or admixture with excipients suitable for either enteral or parenteral application. Preferred are tablets and gelatin capsules comprising the active ingredient together with (a) diluents, e.g. lactose, dextrose, sucrose, mannitol, sorbitol, cellulose and/or glycine, (b) lubricants, e.g. silica, talcum, stearic acid, its magnesium or calcium salt and/or polyethyleneglycol, for tablets also (c) binders, e.g. magnesium aluminum silicate, starch paste, gelatin, tragacanth, methylcellulose, sodium carboxymethylcellulose and/or polyvinylpyrrolidone, if desired, (d) disintegrants, e.g. starches, agar, alginic acid or its sodium salt, enzymes of the binders or effervescent mixtures and/or (e) adsorbents, colorants, flavors and sweetners. Injectable compositions are preferably aqueous isotonic solutions or suspensions, and suppositories are advantageously fatty emulsions or suspensions. They may be sterilized and/or contain adjuvants, such as preserving, stabilizing, wetting or emulsifying agents, solution promoters, salts for regulating the osmotic pressure and/or buffers. They may also contain other therapeutically valuable substances, e.g. antihypertensives and/or psychotherapeutics, as illustrated by U.S. Pat. Nos. 3,288,678, 3,379,612, 3,499,082 and 3,515,786. Said pharmaceutical compositions are prepared according to conventional mixing, granulating or coating methods respectively and contain about 0.1 to 75%, preferably about 1 to 50% of the active ingredient.

The following examples illustrating the invention are not to be construed as being limitations thereon. Temperatures are given in degrees Centigrade and all parts wherever given are parts by weight.

EXAMPLE 1

The mixture of 1.9 g of 4-(4-acetamidophenoxy)-3-n-butylamino-5-sulfamoylbenzoic acid and 19 ml of 2N aqueous sodium hydroxide is refluxed for one hour under nitrogen. After cooling to room temperature it is filtered, the filtrate acidified with glacial acetic acid to a pH of 4-5, the precipitate formed filtered off, washed with water and recrystallized from 50% aqueous ethanol, to yield the 4-(4-aminophenoxy)-3-n-butylamino-5-sulfamoylbenzoic acid of the formula

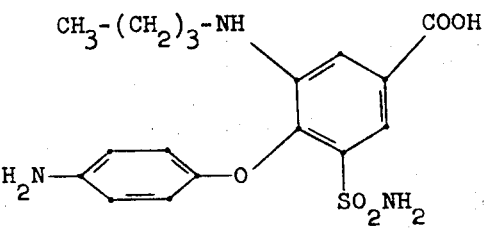

melting at 264° with decomposition.

The starting material is prepared as follows: The mixture of 14 g of 4-chloro-3-nitro-5-sulfamoylbenzoic acid, 200 ml of 1N aqueous sodium bicarbonate and 15.9 g of 4-acetamidophenol is heated to about 95°–100°C for 21 hours while stirring under nitrogen. It is cooled to room temperature and made strongly acidic with concentrated hydrochloric acid. The precipitate formed is filtered off, to yield the 4-(4-acetamidophenoxy)-3-nitro-5-sulfamoylbenzoic acid, which after trituration with aqueous ethanol melts at 293° with decomposition.

The mixture of 9.5 g thereof, 100 ml of water, 1 g of sodium hydroxide and 2.5 g of 10% palladium on charcoal is hydrogenated at room temperature and 2.8 atm until the theoretical amount of hydrogen has been absorbed. It is filtered, the filtrate acidified with concentrated hydrochloric acid, the precipitate formed filtered off, washed with water and triturated with aqueous ethanol, to yield the 4-(4-acetamidophenoxy)-3-amino-5-sulfamoylbenzoic acid melting at 305° with decomposition.

5.5 g thereof are dissolved in 10 ml of N aqueous sodium hydroxide and 30 ml of water, the pH of the solution kept at 7.4 by the dropwise addition of 4N aqueous sodium hydroxide while 2 g of 1-bromo-2-butene are added at room temperature and the mixture stirred for about 17 hours. The mixture is filtered, the filtrate acidified to pH = 4 with glacial acetic acid and the precipitate formed filtered off. It is taken up in 10 ml of 50% hot aqueous ethanol, the mixture diluted with 25 ml of ethanol-water (1:2) and the precipitate formed in the cold filtered off, to yield the 4-(4-acetamidophenoxy)-3-(2-butenylamino)-5-sulfamoylbenzoic acid, melting at 255°–257° with decomposition.

The solution of 1.9 g thereof in 150 ml of anhydrous ethanol is hydrogenated over 0.2 g of platinum oxide at room temperature and atmospheric pressure. After the theoretical amount of hydrogen has been absorbed, the mixture is filtered and the filtrate evaporated, to yield the 4-(4-acetamidophenoxy)-3-n-butylamino-5-sulfamoylbenzoic acid.

EXAMPLE 2

The mixture of 0.9 g of 4-(4-acetamidophenoxy)-3-(2-butenylamino)-5-sulfamoylbenzoic acid and 9 ml of 2N aqueous sodium hydroxide is refluxed for one hour under nitrogen. After cooling to room temperature it is filtered, the filtrate acidified with glacial acetic acid to pH = 4 and the supernatant solution decanted off. It is further acidified with concentrated hydrochloric acid to pH = 1 and the precipitate formed after cooling filtered off and washed with cold water, to yield the 4-(4-aminophenoxy)-3-(2-butenylamino)-5-sulfamoylbenzoic acid hydrochloride of the formula

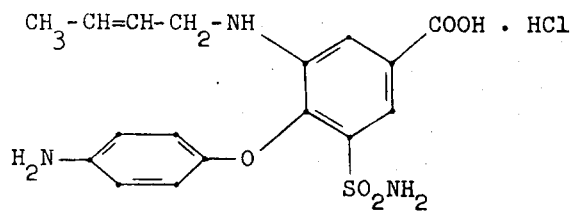

melting at 271° with decomposition.

EXAMPLE 3

The mixture of 2.8 g of 4-(4-acetamidophenylmercapto)-3-n-butylamino-5-sulfamoylbenzoic acid and 28 ml of 2N aqueous sodium hydroxide is refluxed for one hour under nitrogen. After cooling to room temperature it is filtered, the filtrate acidified with glacial acetic acid to a pH of 4–5, the precipitate formed filtered off, washed with water and recrystallized from 50% aqueous ethanol, to yield the 4-(4-aminophenylmercapto)-3-n-butylamino-5-sulfamoylbenzoic acid of the formula

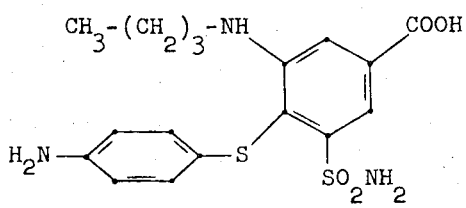

melting at 236° with decomposition.

The starting material is prepared as follows: The mixture of 19.6 g of 4-chloro-3-nitro-5-sulfamoylbenzoic acid, 280 ml of N aqueous sodium hydroxide and 11.8 g of 4-acetamidothiophenol is stirred for 24 hours at room temperature under nitrogen. It is filtered, the filtrate made strongly acidic with concentrated hydrochloric acid, the precipitate formed filtered off and recrystallized from 50% aqueous ethanol, to yield the 4-(4-acetamidophenylmercapto)-3-nitro-5-sulfamoylbenzoic acid, melting at 168°.

8.2 g thereof are added portionwise to the mixture of 16 g of iron powder, 1.7 g of ammonium chloride, 70 ml of water and 0.8 ml of N hydrochloric acid while stirring. After heating it for four hours at the steam bath it is filtered hot, the precipitate taken up in 200 ml of N aqueous sodium hydroxide and the solution filtered. The filtrates are acidified with concentrated hydrochloric acid and the precipitate formed recrystallized from 50% aqueous ethanol, to yield the 4-(4-acetamidophenylmercapto)-3-amino-5-sulfamoylbenzoic acid melting at 207°.

3.8 g thereof are dissolved in 50 ml of water containing 0.4 g of sodium hydroxide, the pH of the solution kept at 7.4 by the dropwise addition of 4N aqueous sodium hydroxide and 1.4 g of 1-bromo-2-butene are added at room temperature. The mixture is stirred for about one hour, filtered, the filtrate acidified to a pH of 4–5 with glacial acetic acid and the precipitate formed filtered off. It is recrystallized from aqueous ethanol, to yield the 4-(4-acetamidophenylmercapto)-3-(2-butenylamino)-5-sulfamoylbenzoic acid, melting at 148°.

The solution of 2.75 g thereof in 750 ml of anhydrous ethanol is hydrogenated over 0.2 g of platinum oxide at room temperature and atmospheric pressure. After the theoretical amount of hydrogen has been absorbed, the mixture is filtered hot and the filtrate evaporated, to yield the 4-(4-acetamidophenylmercapto)-3-n-butylamino-5-sulfamoylbenzoic acid.

EXAMPLE 4

The mixture of 1.2 g of 4-(4-acetamidophenylmercapto)-3-(2-butenylamino)-5-sulfamoylbenzoic acid and 12 ml of 2N aqueous sodium hydroxide is refluxed for one hour under nitrogen. After cooling to room temperature it is filtered, the filtrate acidified with glacial acetic acid to a pH of 4-5 and the precipitate formed filtered off. It is washed with water and recrystallized from 50% aqueous ethanol, to yield the 4-(4-aminophenylmercapto)-3-(2-butenylamino)-5-sulfamoylbenzoic acid, melting at 242°.

EXAMPLE 5

The mixture of 1.4 g of 4-(4-acetamidophenoxy)-3-benzylamino-5-sulfamoylbenzoic acid and 14 ml of 2N aqueous sodium hydroxide is refluxed for one hour under nitrogen. After cooling to room temperature it is filtered and the filtrate acidified with glacial acetic acid to pH = 4. The precipitate formed is filtered off and recrystallized from aqueous ethanol, to yield the 4-(4-aminophenoxy)-3-benzylamino-5-sulfamoylbenzoic acid of the formula

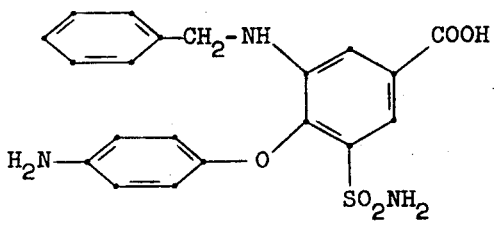

melting at 272° with decomposition.

The starting material is prepared as follows: To the mixture of 3.6 g of 4-(4-acetamidophenoxy)-3-amino-5-sulfamoylbenzoic acid, 10 ml of water and the sufficient amount of N aqueous sodium hydroxide to reach a pH = 7.4, 1.3 g of benzyl chloride are added while stirring at 30°. The mixture is stirred for 16 hours at room temperature, during which time 4N aqueous sodium hydroxide is added dropwise to keep said pH value. It is filtered, the filtrate acidified with glacial acetic acid and the precipitate formed filtered off, to yield the 4-(4-acetamidophenoxy)-3-benzylamino-5-sulfamoylbenzoic acid which, on recrystallization from aqueous ethanol, melts at 255° with decomposition.

EXAMPLE 6

The mixture of 2.5 g of 4-(4-acetamido-3-tolyloxy)-3-benzylamino-5-sulfamoylbenzoic acid and 25 ml of 2N aqueous sodium hydroxide is refluxed for seven hours under nitrogen. After cooling it is filtered, the filtrate acidified to a pH of 4-5 with glacial acetic acid, the precipitate formed filtered off, washed with water and recrystallized from 50% aqueous ethanol, to yield the 4-(4-amino-3-tolyloxy)-3-benzylamino-5-sulfamoylbenzoic acid of the formula

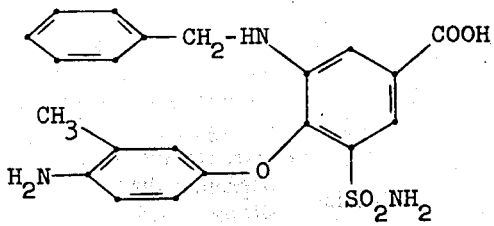

melting at 266°.

The starting material is prepared as follows: The mixture of 14 g of 4-chloro-3-nitro-5-sulfamoylbenzoic acid, 200 ml of water, 16.8 g of sodium bicarbonate and 17.3 g of 4-acetamido-m-cresol is stirred for 14 hours at 90°–95° under nitrogen. After cooling it is acidified with concentrated hydrochloric acid, the supernatant solution decanted off and the residue taken up in 70 ml of hot ethanol, followed by 70 ml of water and the precipitate formed in the cold filtered off, to yield the 4-(4-acetamido-3-tolyloxy)-3-nitro-5-sulfamoylbenzoic acid melting at 238°–240°.

The mixture of 6.3 g thereof, 70 ml of water and 8 ml of 2N aqueous sodium hydroxide is hydrogenated over 1 g of 10% palladium on charcoal until the theoretical amount of hydrogen has been absorbed. It is filtered, the filtrate acidified with hydrochloric acid, the precipitate formed filtered off and recrystallized from 75% aqueous ethanol, to yield the 4-(4-acetamido-3-tolyloxy-3-amino-5-sulfamoylbenzoic acid melting above 280°.

The solution of 3.7 g thereof in 10 ml of water and 5 ml of N aqueous sodium hydroxide is adjusted to pH = 7.4 by the addition of 4N aqueous sodium hydroxide after which 1.3 g of benzylchloride are added while stirring at room temperature under nitrogen. During the following 41 hours water is added to facilitate stirring. The mixture is filtered, the filtrate acidified with glacial acetic acid to a pH 4–5 and the precipitate formed recrystallized from 50% aqueous ethanol, to yield the 4-(4-acetamido-3-tolyloxy)-3-benzylamino-5-sulfamoylbenzoic acid melting at 203°.

EXAMPLE 7

The mixture of 2.2 g of 4-(4-acetamidophenylmercapto)-3-benzylamino-5-sulfamoylbenzoic acid and 22 ml of 2N aqueous sodium hydroxide is refluxed for one hour under nitrogen. After cooling it is filtered, the filtrate acidified with glacial acetic acid to pH = 4. The precipitate formed is filtered off and recrystallized from 50% aqueous ethanol, to yield the 4-(4-aminophenylmercapto)-3-benzylamino-5-sulfamoylbenzoic acid melting at 254°–256°.

The starting material is prepared as follows: The solution of 4-(4-acetamidophenylmercapto)-3-amino-5-sulfamoylbenzoic acid if 50 ml of water containing 0.4 g of sodium hydroxide is adjusted to pH = 7.4 by the addition of 4N aqueous sodium hydroxide, whereupon 1.3 g of benzylchloride are added while stirring under nitrogen. As soon as the pH remains constant the mixture is filtered and the filtrate acidified with glacial acetic acid to a pH of 4–5. The precipitate formed is recrystallized from 50% aqueous ethanol, to yield the 4-(4-acetamidophenylmercapto)-3-benzylamino-5-sulfamoylbenzoic acid melting at 255°–258°.

EXAMPLE 8

The mixture of 1.1 g of 4-(4-acetamidophenoxy)-3-furfurylamino-5-acetylsulfamoylbenzoic acid and 11 ml of 2N aqueous sodium hydroxide is refluxed for two hours under nitrogen. After cooling to room temperature it is filtered, the filtrate acidified with glacial acetic acid to a pH of 4-5 and the precipitate formed filtered off. It is recrystallized from 70% aqueous ethanol, to yield the 4-(4-aminophenoxy)-3-furfurylamino-5-sulfamoylbenzoic acid melting at 233°–235°.

The starting material is prepared as follows: The mixture of 12.5 g of 4-(4-acetamidophenoxy)-3-nitro-5-sulfamoylbenzoic acid and 125 ml of acetic anhydride is refluxed for two hours under nitrogen and evaporated under reduced pressure. The residue is taken up in 125 ml of 2N aqueous sodium hydroxide and 25 ml of water, the solution washed with diethyl ether, filtered and the filtrate acidified with concentrated hydrochloric acid and the precipitate recrystallized from 33 and 50% aqueous ethanol, to yield the 4-(4-acetamidophenoxy)-3-nitro-5-acetylsulfamoylbenzoic acid decomposing at about 240°. The solution of 10.5 g thereof in 100 ml of water and 22 ml of 2N aqueous sodium hydroxide is hydrogenated over 2.5 g of 10% palladium on charcoal until the theoretical amount of hydrogen has been absorbed. The mixture is filtered, the filtrate acidified with concentrated hydrochloric acid and the precipitate recrystallized from aqueous ethanol, to yield the 4-(4-acetamidophenoxy)-3-amino-5-acetylsulfamoylbenzoic acid melting at 305°–306° with decomposition.

The mixture of 2.4 g thereof and 24 ml of furfural is heated to 90°–95° for 18 hours while stirring under nitrogen. It is filtered hot and the filtrate evaporated under reduced pressure, to yield the corresponding Schiff's base. To the solution of 1.5 g thereof in 80 ml of ethanol, 3.3 g of sodium borohydride are added portionwise during 20 minutes while stirring and cooling with ice. Thereupon the mixture is stirred for 18 hours under nitrogen, 1.8 g of additional sodium borohydride are added and the mixture stirred 90 minutes longer. Thereupon 130 ml of water are added, the mixture concentrated under reduced pressure, the concentrate acidified with concentrated hydrochloric acid and the precipitate recrystallized from 50% aqueous ethanol, to yield the 4-(4-acetamidophenoxy)-3-furfurylamino-5-acetylsulfamoylbenzoic acid melting at 250° with decomposition.

EXAMPLE 9

The mixture of 2.3 g of 4-(4-acetamidophenylmercapto)-3-furfurylamino-5-sulfamoylbenzoic acid and 23 ml of 2N aqueous sodium hydroxide is refluxed for one hour under nitrogen. After cooling to room temperature it is acidified to pH = 5 and the precipitate formed filtered off. It is dissolved in 25 ml of 50% hot aqueous ethanol, the solution cooled to room temperature and decanted from some amorphous substance. The supernatant solution is allowed to stand at room temperature for a longer period of time, the precipitate formed filtered off and this recrystallization procedure repeated several times, to yield the 4-(4-aminophenylmercapto)-3-furfurylamino-5-sulfamoylbenzoic acid, starting to melt at about 125°.

The starting material is prepared as follows: The mixture of 2 g of 4-(4-acetamidophenylmercapto)-3-amino-5-sulfamoylbenzoic acid, 1 g of furfural and 20 ml of diethyleneglycol dimethyl ether is heated to 105° for 22 hours while stirring under nitrogen. It is evaporated under reduced pressure, the residue taken up in 75 ml of ethanol and 1 g of sodium borohydride is added portionwise while stirring at room temperature under nitrogen. After stirring overnight, 75 ml of water are added and the mixture is filtered. The filtrate is concentrated under reduced pressure, the concentrate acidified with concentrated hydrochloric acid and the precipitate formed filtered off, to yield the 4-(4-acetamidophenylmercapto)-3-furfurylamino-5-sulfamoylbenzoic acid.

EXAMPLE 10

The mixture of 2 g of 4-(4-acetamidophenylmercapto)-3-(2-methylallylamino)-5-sulfamoylbenzoic acid and 20 ml of 2 N aqueous sodium hydroxide is refluxed for 1 hour under nitrogen. After cooling it is filtered and the filtrate acidified with acetic acid to a pH of 4–5. The precipitate formed is filtered off and recrystallized from aqueous ethanol, to yield the 4-(4-aminophenylmercapto)-3-(2-methylallylamino)-5-sulfamoylbenzoic acid melting at 237°–240°.

The starting material is prepared as follows: To the solution of 3.81 g of 4-(4-acetamidophenylmercapto)-3-amino-5-sulfamoylbenzoic acid in 25 ml of water and about 2 ml of 4 N aqueous lithium hydroxide (to adjust the pH to 7.2), the solution of 2 g of 2-methylallyliodide in 2 ml of ethanol is added at room temperature while stirring and maintaining the pH between 6.7 and 7.0 with lithium hydroxide, and diluting the mixture with 10 ml of ethanol. After 23 hours (and the consumption of about 65% of the theoretical amount of lithium hydroxide) the mixture is washed with diethyl ether and acidified with hydrochloric acid. The precipitate formed is filtered off and recrystallized from aqueous ethanol, to yield the 4-(4-acetamidophenylmercapto)-3-(2-methylallylamino)-5-sulfamoylbenzoic acid melting at 193°–195°.

EXAMPLE 11

The mixture of 3.5 g of 4-(4-acetamidophenylmercapto)-3-isobutylamino-5-sulfamoylbenzoic acid, 35 ml of 2 N aqueous sodium hydroxide and some colloidal platinum is refluxed for 1 hour under nitrogen, during which time the platinum coagulates. After cooling it is filtered, the filtrate acidified with acetic acid to a pH of 4–5, the precipitate formed is filtered off and recrystallized from aqueous ethanol, to yield the 4-(4-aminophenylmercapto)-3-isobutylamino-5-sulfamoylbenzoic acid melting at 250°–252°.

The starting material is prepared as follows: The mixture of 3.5 g of 4-(4-acetamidophenylmercapto)-3-(2-methylallylamino)-5-sulfamoylbenzoic acid, 200 ml of 90% aqueous ethanol and 0.25 g of platinum oxide is hydrogenated at room temperature and atmospheric pressure until 275 ml of hydrogen have been absorbed. It is filtered, the filtrate evaporated, both residues are dissolved in aqueous sodium carbonate, the solution treated with charcoal, filtered through filter-cellulose and the filtrate, still containing platinum, acidified with hydrochloric acid. The precipitate, consisting of 4-(4-acetamidophenylmercapto)-3-isobutylamino-5-sulfamoylbenzoic acid and colloidal platinum, is used as such without purification.

EXAMPLE 12

The mixture of 8.5 g of 4-(4-acetamidophenylmercapto)-3-di-(2-butenyl)-amino-4-sulfamoylbenzoic acid and 85 ml of 2 N aqueous sodium hydroxide is refluxed for 1 hour under nitrogen. After cooling it is filtered, the filtrate acidified with glacial acetic acid to a pH of 4–5 and the precipitate formed filtered off. It is washed with water, dried, dissolved in 10 ml of hot 50% aqueous ethanol and the solution cooled and diluted with water until precipitation occurs. After standing the precipitate is filtered off, washed with water and dried, to yield the 4-(4-aminophenylmercapto)-3-di- (2-butenyl)-amino-5-sulfamoylbenzoic acid of the formula

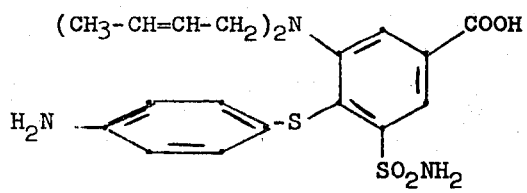

The starting material is prepared as follows: The combined ethanolic motherliquors of several crops of the 4-(4-acetamidomethylmercapto)-3-(2-butenylamino)-5-sulfamoylbenzoic acid (obtained according to Example 3) are concentrated and allowed to stand overnight at room temperature, during which time the corresponding 3-di-(2-butenyl)-amino by-product crystallizes. It is filtered off, washed with water, dried and used as such without further purification.

EXAMPLE 13

The mixture of 0.6 g of 4-(4-acetamidophenylmercapto)-3-cyclopropylmethylamino-5-sulfamoylbenzoic acid, 3 ml of water and 6 ml of 2 N aqueous sodium hydroxide is refluxed for 2 hours under nitrogen. After cooling it is filtered, the filtrate acidified with glacial acetic acid to pH 4-5, the precipitate separated, washed with water and recrystallized from 66% aqueous ethanol, to yield the 4-(4-aminophenylmercapto)-3-cyclopropylmethylamino-5-sulfamoylbenzoic acid melting at 221°-223°.

The starting material is prepared as follows: To the mixture of 3.8 g of 4-(4-acetamidophenylmercapto)-3-amino-5-sulfamoylbenzoic acid, 20 ml of water, 15 ml of ethanol and 2 ml of 4 N aqueous lithium hydroxide, 2.2 g of cyclopropylmethyl bromide are added while stirring and the pH of the mixture adjusted with lithium hydroxide to 7.0 during 24 hours. Thereupon, it is filtered, the filtrate diluted with water, washed with diethyl ether and acidified with concentrated hydrochloric acid. The precipitate formed is filtered off and recrystallized from aqueous ethanol, to yield the 4-(4-acetamidophenylmercapto)-3-cyclopropylmethylamino-5-sulfamoylbenzoic acid melting at 200°-204°.

EXAMPLE 14

The mixture of 1.5 g of 4-(4-acetamidophenylmercapto)-3-cinnamylamino-5-sulfamoylbenzoic acid and 15 ml of 2 N aqueous sodium hydroxide is refluxed for 80 minutes under nitrogen. After cooling it is washed with diethyl ether, acidified with glacial acetic acid to a pH of 4-5, the precipitate collected and recrystallized from 75% aqueous ethanol, to yield the 4-(4-aminophenylmercapto)-3-cinnamylamino-5-sulfamoylbenzoic acid of the formula

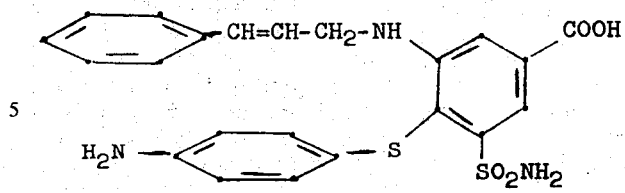

melting at 228°-232° with decomposition.

The starting material is prepared as follows: To the solution of 3.81 g of 4-(4-acetamidophenylmercapto)-3-amino-5-sulfamoylbenzoic acid, 25 ml of water and 2 ml of 4 N aqueous lithium hydroxide, the solution of 2 g of cinnamyl bromide in 2 ml of ethanol is added while stirring and maintaining a pH of 7.2 by addition of aqueous lithium hydroxide. After about 45 minutes the pH stabilizes and the turbid solution is washed with diethyl ether. It is acidified with hydrochloric acid and the supernatant solution decanted off the separated oil, which crystallizes upon trituration with water. It is recrystallized twice from 50% aqueous ethanol, to yield the 4-(acetamidophenylmercapto)-3-cinnamylamino-5-sulfamoylbenzoic acid melting at 248° with decomposition.

EXAMPLE 15

The mixture of 1.5 g of 4-(3-acetamidophenoxy)-3-n-butylamino-5-sulfamoylbenzoic acid and 15 ml of 2 N aqueous sodium hydroxide is refluxed for 5 hours under nitrogen. After cooling it is filtered, the filtrate acidified with glacial acetic acid and hydrochloric acid to a pH of 2-3, the precipitate collected and recrystallized from ethanol, to yield the 4-(3-aminophenoxy)-3-n-butylamino-5-sulfamoylbenzoic acid of the formula

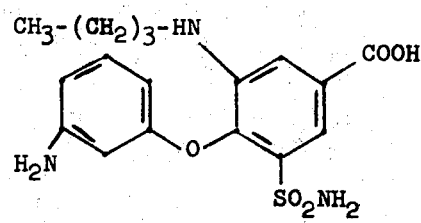

melting at 240°-243°.

The starting material is prepared as follows: The mixture of 14 g of 4-chloro-3-nitro-5-sulfamoylbenzoic, 200 ml of water, 16.8 g of sodium bicarbonate and 15.9 g of 3-acetamidophenol is heated to 90°-95° for 10 hours while stirring under nitrogen. It is cooled to room temperature, strongly acidified with hydrochloric acid, the preicipitate collected and recrystallized twice from aqueous ethanol to yield the 4-(3-acetamidophenoxy)-3-nitro-5-sulfamoylbenzoic melting at 265°-270° with decomposition.

The mixture of 5.8 g thereof, 120 ml of water, 0.65 g of lithium hydroxyde hydrate and 1.5 g of 10% palladium on charcoal is hydrogenated at room temperature untill the hydrogen up-take ceases. It is filtered, the filtrate acidified with hydrochloric acid to pH = 2, the precipitate collected and recrystallized from 100 ml of 75% aqueous ethanol, to yield the 4-(3-acetamidophenoxy)-3-amino-5-sulfamoylbenzoic acid melting at 295° with decomposition.

To the stirred mixture of 3.65 g thereof, 0.42 g of lithium hydroxide and 35 ml of water, 1.35 g of 1-bromo-2-butene are added while stirring and keeping the pH of the solution at about 8 with 4 N aqueous lithium hydroxide. After one hour it is filtered, the filtrate acidified with glacial acetic acid to pH = 5, the precipitate collected and recrystallized from ethanol, to yield the 4-(3-acetamidophenoxy)-3-(2-butenylamino)-5-sulfamoylbenzoic acid melting at 198°–202° with decomposition.

The mixture of 1.7 g thereof, 65 ml of ethanol, 15 ml of water and 0.2 g of platinum oxide is hydrogenated at room temperature and atmospheric pressure until 115 ml of hydrogen have been absorbed. It is filtered and the filtrate evaporated under reduced pressure, to yield the 4-(3-acetamidophenoxy)-3-n-butylamino-5-sulfamoylbenzoic acid melting at 235°–240°.

EXAMPLE 16

To the solution of 1.52 g of 4-(4-acetamidophenylmercapto)-3-amino-5-sulfamoylbenzoic acid in 600 ml of dimethylformamide, 40 g of butyraldehyde and 1.60 g of molecular sieves [$Na_{12}(AlSiO_4)_{12} \cdot 27 H_2O$], 36 g of sodium cyanoborohydride are added while stirring under nitrogen and keeping the temperature between about 20 and 30° for one hour. After stirring the mixture for 68 hours at room temperature, 6 lt of water are added, followed by 110 ml of concentrated hydrochloric acid and stirring is continued for one hour. The precipitate formed is filtered off, washed with water, dissolved in 1.2 lt of 2N aqueous sodium hydroxide and the solution refluxed for 2 hours under nitrogen. After cooling to room temperature it is filtered and the filtrate combined with 250 ml of glacial acetic acid. The precipitate formed is collected, 333 g thereof are dissolved in 2.8 lt of hot, 80% aqueous acetonitrile, the solution filtered, the filter washed with 500 ml more of said acetonitrile and the filtrate diluted with 3.3 lt of hot water. The precipitate formed at 14° is filtered off, taken up in 2.15 lt of hot, 90% aqueous ethanol and the solution diluted with 2.5 lt of hot water. The solids separated after cooling are collected and washed with water, to yield the 4-(4-aminophenylmercapto)-3-n-butylamino-5-sulfamoylbenzoic acid melting at 232°–234°, it is identical with that obtained according to Example 3.

493 g thereof are disolved in 2.5 lt of anhydrous ethanol containing 50 g of sodium hydroxide while stirring and warming. It is diluted with 2 lt of ethanol-ethyl acetate (1:3) and stirring is continued for 1.5 hours at room temperature. The precipitate formed is filtered off washed with 400 ml of said ethanolic ethyl acetate and dried under reduced pressure, to yield the corresponding sodium salt dihydrate melting at about 190°.

EXAMPLE 17

The mixture of 5.1 g of 4-(4-acetamidophenylmercapto)-3-n-butylamino-5-n-butylsulfamoyl benzoic acid and 75 ml of 2N aqueous sodium hydroxide is refluxed for 2 hours under nitrogen and filtered after cooling to room temperature. The filtrate is acidified with glacial acetic acid to pH=4, the precipitate filtered off and recrystallized several times from aqueous ethanol. It is dissolved in the minimum amount of 2N aqueous sodium hydroxide, chromatographed on silica gel and the column eluted with ethyl acetate-methanol-saturated aqueous amonia (65: 25: 10), to yield the 4-(4-amino-phenylmercapto)-3-n-butylamino-5-n-butylsulfamoylbenzoic acid of the formula

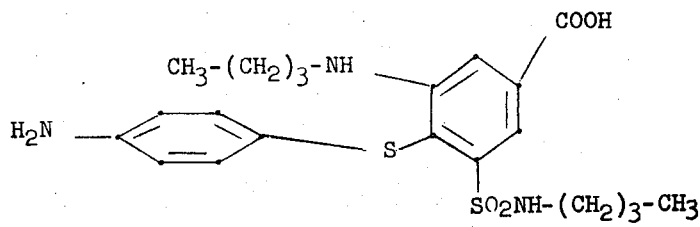

melting at 198°–200°.

The starting material is prepared as follows: To the stirred solution 7.3 g of n-butylamine, 8 g of sodium hydroxide in 200 ml of water, 30 g of 4-chloro-5-chlorosulfonyl-3-nitrobenzoic acid are added portionwise while keeping the temperature between 0° and 5°. After 1/2 hour the mixture is allowed to warm to room temperature for 2 hours. The supernatant solution is filtered, the filtrate combined with 25 ml of 2N of hydrochloric acid, the precipitate formed collected and recrystallized from aqueous ethanol, to yield the 4-chloro-3-nitro-5-n-butylsulfamoylbenzoic acid melting at 199°–201°.

The mixture of 13.4 g thereof, 160 ml of N aqueous sodium hydroxide and 6.7 g of 4-acetamidothiophenol is stirred for 24 hours at room temperature under nitrogen. It is filtered, the filtrate made strongly acidic with concentrated hydrochloric acid, the precipitate formed filtered off and recrystallized from 50% aqueous ethanol, to yield the 4-(4-acetamidophenylmercapto-3-nitro-5-n-butylsulfamoylbenzoic acid, melting at 220°–222°.

13.9 g thereof are added portionwise to the mixture of 24 g of iron powder, 2.5 g of ammonium chloride, 105 ml of water and 1.2 ml of N hydrochloric acid while stirring. After heating it for two hours at the steam bath it is filtered hot, the precipitate taken up in 100 ml of N aqueous sodium hydroxide and the solution filtered. The filtrates are acidified with concentrated hydrochloric acid and the precipitate formed recrystallized from 33% aqueous ethanol, to yield the 4-(4-acetamidophenylmercapto)-3-amino-5-n-butylsulfamoylbenzoic acid melting at 228°–229°.

8.75 g thereof are disolved in 30 ml of dimethyl formamide and 2 g of butyraldehyde, 8 g of molecular sieves (Example 16) and 1.8 g of sodium cyanoborohydride are added and the mixture stirred at room temperature for 72 hours under nitrogen. It is decanted, poured into 300 ml of water and the mixture extracted with ethyl acetate. The extract is dried and filtered, to yield the 4-(4-acetamidophenylmercapto)-3-n-butylamino-5-n-butylsulfamoylbenzoic acid.

EXAMPLE 18

Preparation of 10,000 tablets each containing 5 mg of the active ingredient:

| Formula: | |
|---|---|
| 4-(4-aminophenylmercapto)-3-n-butylamino-5-sulfamoy'benzoic acid | 50.0 g |
| Lactose | 1,207.0 g |
| Corn starch | 75.0 g |
| Polyethylene glycol 6.000 | 75.0 g |
| Talcum powder | 75.0 g |
| Magnesium stearate | 18.0 g |
| Purified water | q.s. |

PROCEDURE

All the powders are passed through a screen with openings of 0.6 mm. Then the drug substance, lactose, talcum, magnesium stearate and half of the starch are mixed in a suitable mixer. The other half of the starch is suspended in 40 ml of water and the suspension added to the boiling solution of the polyethylene glycol in 150 ml of water. The paste formed is added to the powders which are granulated, if necessary, with an additional amount of water. The granulate is dried overnight at 35°, broken on a screen with 1.2 mm openings and compressed into tablets using concave punches with 6.4 mm diameter, uppers bisected.

Similarly, 5 mg tablets are prepared from the remaining compounds of the invention, e.g. those illustrated by the previous examples.

I claim:
1. A 4-phenylether of the 3-amino-5-sulfamoylbenzoic acid corresponding to the formula

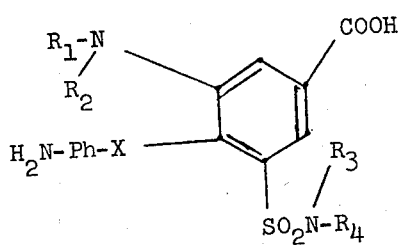

in which $R_1$ is lower alkyl, lower alkenyl, cycloalkyl or cycloalkyl-lower alkyl each of which with 3 to 7 ring-carbon atoms, $R_2$ is hydrogen, lower alkyl or lower alkenyl $R_3$ is hydrogen or lower alkyl, X is oxygen or sulfur, Ph is unsubstituted phenylene or phenylene substituted by one member of lower alkyl, and $R_4$ is hydrogen or lower alkyl, or the lower alkyl esters or therapeutically useful ammonium, alkali or alkaline earth metal or acid addition salts thereof.

2. A compound as claimed in claim 1, in which formula $R_1$ is lower alkyl, lower alkenyl, or (monocyclic, 3 to 7 ring-membered cycloalkyl) $-C_mH_{2m}$, Ph is 1,2-, 1,3-, or 1,4-phenylene, unsubstituted or substituted by one member of a lower alkyl, m is an integer from 0 to 4, $R_2$ is hydrogen, lower alkyl or lower alkenyl, $R_3$ is hydrogen or lower alkyl, X is oxygen or sulfur, and $R_4$ is hydrogen or lower alkyl, or the lower alkyl esters, or therapeutically useful ammonium, alkali or alkaline earth metal or acid addition salts thereof.

3. A compound as claimed in claim 2 and corresponding to the formula

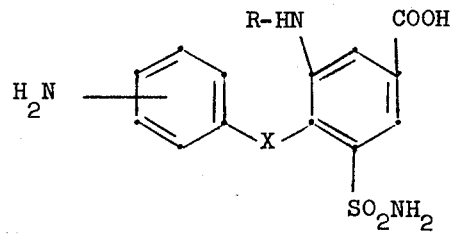

wherein R is alkyl or alkenyl with 3 to 7 carbon atoms, (3 to 7 ring-membered cycloalkyl,) -methyl or -ethyl and X is oxygen or sulfur, or therapeutically useful ammonium, alkali metal or acid addition salts thereof.

4. A compound as claimed in claim 3, in which formula R is alkyl or 2-alkenyl with 4 to 5 carbon atoms or cyclopropylmethyl and X is oxygen or sulfur, or therapeutically useful ammonium, alkali metal or acid addition salts thereof.

5. A compound as claimed in claim 3 and being the 4-(4-aminophenylmercapto)-3-(n- or i-butyl or cyclopropylmethyl)-amino-5-sulfamoylbenzoic acid.

6. Therapeutically useful ammonium, alkali metal or acid addition salts of the compounds claimed in claim 5.

7. A compound as claimed in claim 3 and being the 4-(4-aminophenylmercapto)-3-n-butylamino-5-sulfamoyl benzoic acid or its sodium salt.

* * * * *